United States Patent
Tegg et al.

(10) Patent No.: US 11,890,427 B2
(45) Date of Patent: Feb. 6, 2024

(54) MEDICAL DEVICE WITH NON-METALLIC REINFORCING LAYER

(71) Applicant: St. Jude Medical, Cardiology Division, Inc., St. Paul, MN (US)

(72) Inventors: Troy T. Tegg, Elk River, MN (US); Dale E. Just, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 716 days.

(21) Appl. No.: 15/860,759

(22) Filed: Jan. 3, 2018

(65) Prior Publication Data

US 2018/0185610 A1 Jul. 5, 2018

Related U.S. Application Data

(60) Provisional application No. 62/441,701, filed on Jan. 3, 2017.

(51) Int. Cl.
| | |
|---|---|
| *A61M 25/00* | (2006.01) |
| *B29C 63/00* | (2006.01) |
| *B29L 31/00* | (2006.01) |
| *B29C 61/02* | (2006.01) |
| *B29K 309/08* | (2006.01) |
| *B29K 279/00* | (2006.01) |
| *B29C 63/18* | (2006.01) |
| *B29C 63/42* | (2006.01) |
| *A61M 25/01* | (2006.01) |

(52) U.S. Cl.
CPC ...... *A61M 25/005* (2013.01); *A61M 25/0012* (2013.01); *A61M 25/0045* (2013.01); *A61M 25/0108* (2013.01); *B29C 61/025* (2013.01); *B29C 63/0069* (2013.01); *B29C 63/18* (2013.01); *B29C 63/42* (2013.01); *B29K 2279/08* (2013.01); *B29K 2309/08* (2013.01); *B29L 2031/7542* (2013.01)

(58) Field of Classification Search
CPC ............ A61M 25/0045; A61M 25/005; A61M 2205/0238; A61M 25/0012; A61B 1/00165; A61B 1/00167; A61B 1/0017; A61B 1/07; B29C 61/025; B29C 63/0069; B29C 63/18; B29K 2309/08
See application file for complete search history.

(56) References Cited

U.S. PATENT DOCUMENTS

| | | | | |
|---|---|---|---|---|
| 3,498,286 | A | * 3/1970 | Polanyi et al. .... | A61B 1/00071 600/325 |
| 3,924,632 | A | 12/1975 | Cook | |
| 5,116,317 | A | * 5/1992 | Carson, Jr. ......... | A61B 1/00082 600/116 |
| 6,257,280 | B1 | * 7/2001 | Marena ................ | B29D 23/001 138/125 |
| 6,989,486 | B2 | 1/2006 | Lovoi et al. | |

(Continued)

*Primary Examiner* — Shefali D Patel
(74) *Attorney, Agent, or Firm* — Wiley Rein LLP

(57) ABSTRACT

A medical device, such as an electrophysiology catheter, has an elongate body including a wall. A reinforcing layer is encapsulated in the wall. The reinforcing layer includes one or more reinforcing fibers having glass cores and polymer claddings. In embodiments, the one or more reinforcing fibers are non-magnetically-susceptible and non-electrically-conductive, facilitating use of the medical device in connection with procedures such as magnetic resonance imaging ("MRI").

6 Claims, 3 Drawing Sheets

(56) References Cited

U.S. PATENT DOCUMENTS

| | | |
|---|---|---|
| 7,105,607 B2 | 9/2006 | Chen |
| 8,251,976 B2 * | 8/2012 | Zhou ................ A61M 25/0053 604/523 |
| 8,734,699 B2 | 5/2014 | Heideman et al. |
| 8,864,744 B2 | 10/2014 | Howat et al. |
| 8,983,255 B2 * | 3/2015 | Shinji ................ A61B 1/00167 385/109 |
| 2003/0208142 A1 | 11/2003 | Boudewijn et al. |
| 2009/0080750 A1 | 3/2009 | Krueger et al. |
| 2009/0287183 A1 * | 11/2009 | Bishop ................ A61M 25/104 604/509 |
| 2009/0299446 A1 | 12/2009 | Lovoi et al. |
| 2013/0041447 A1 | 2/2013 | Erb et al. |
| 2014/0155948 A1 | 6/2014 | Walsh et al. |
| 2015/0011837 A1 | 1/2015 | Johnson et al. |
| 2015/0038824 A1 | 2/2015 | Lupotti |
| 2016/0058974 A1 | 3/2016 | Kimmel et al. |

* cited by examiner

MEDICAL DEVICE WITH NON-METALLIC REINFORCING LAYER

CROSS-REFERENCE TO RELATED APPLICATIONS

This application claims the benefit of U.S. provisional application No. 62/441,701, filed 3 Jan. 2017, which is hereby incorporated by reference as though fully set forth herein.

BACKGROUND

The instant disclosure relates to elongate medical devices, such as catheters. In particular, the instant disclosure relates to elongate medical devices including non-magnetically-susceptible, non-electrically-conductive reinforcing layers.

Catheters are used for an ever-growing number of procedures. For example, catheters are used for diagnostic, therapeutic, and ablative procedures, to name just a few examples. In an electrophysiology ("EP") procedure, for example, a catheter may be manipulated through the patient's vasculature and to an intended site for mapping and/or treatment, for example, a site within the patient's heart. A catheter may carry one or more devices, sensors, or surgical instruments, such as electrodes, which may be used for ablation, diagnosis, and/or the like.

The path through the patient's vasculature to the intended site, however, is often long and tortuous. As such, steering forces applied at the proximal end of the catheter (e.g., to a handle that remains outside the body) often must be transmitted over relatively great distances. Accordingly, it is desirable for a catheter to have sufficient axial (e.g., column) strength to be pushed through the patient's vasculature via a force applied at its proximal end ("pushability"). It is also desirable for a catheter to transmit a torque applied at the proximal end to the distal end ("torqueability"). Pushability and torqueability (collectively, "maneuverability") permit a physician to manipulate a catheter to an intended site and then properly orient the catheter.

It is also desirable for a catheter to have sufficient flexibility to substantially conform to the patient's vasculature and yet resist kinking as it does so. Kinking is often the result of a localized failure of the material of the catheter when localized stresses exceed the yield strength of the material.

To provide pushability, torqueability, flexibility, and kink resistance, many extant catheters are made of engineering polymer materials reinforced with metallic wire braiding plaits. Such metallic braid plaits, however, are not desirable for use in certain applications, such as magnetic resonance imaging ("MRI"), because the metallic reinforcing layer can interfere with the imaging and experience self-heating.

BRIEF SUMMARY

Disclosed herein is a method of manufacturing a shaft for a medical device by forming a reinforcing layer into an elongate structure, the reinforcing layer including a plurality of reinforcing fibers, wherein each reinforcing fiber includes a glass core surrounded by a polymer cladding, such as a polyimide cladding. The method can also include: forming an inner layer; forming the reinforcing layer about the inner layer; forming an outer layer about the reinforcing layer; and bonding the inner layer to the outer layer to form a catheter shaft having the reinforcing layer encapsulated therein.

According to aspects of the disclosure, the inner layer includes a first melt-processable polymer, the outer layer includes a second melt-processable polymer, and the bonding step includes heating the inner layer and the outer layer to form a unitary catheter shaft having the reinforcing layer encapsulated therein. A heat-shrink tube can also be formed about the outer layer prior to heating the inner layer and the outer layer.

It is desirable for the plurality of reinforcing fibers to be non-magnetically-susceptible and non-electrically-conductive. They can also be braided together to form the reinforcing layer. In embodiments of the instant disclosure, the overall diameter of each of the plurality of reinforcing fibers does not exceed 65 µm, with the diameter of the glass core being between 50 and 55 µm.

It is also contemplated that the glass core can be doped, for example with germanium.

Also disclosed herein is a shaft for a medical device, including an elongate structure including a reinforcing layer including a plurality of reinforcing fibers, wherein each reinforcing fiber includes a glass core surrounded by a polymer cladding (e.g., a polyimide cladding). The shaft can also include: an inner layer about which reinforcing layer is formed; and an outer layer bonded to the inner layer such that the reinforcing layer is encapsulated within the inner layer and the outer layer.

It is desirable for the plurality of reinforcing fibers to be non-magnetically-susceptible and non-electrically-conductive. They can also be braided together to form the reinforcing layer. In embodiments of the instant disclosure, the overall diameter of each of the plurality of reinforcing fibers does not exceed 65 µm, with the diameter of the glass core being between 50 and 55 µm.

It is also contemplated that the glass core can be doped, for example with germanium.

According to further embodiments disclosed herein, a medical device includes: an elongate body including a wall; and a reinforcing layer encapsulated in the wall, the reinforcing layer including at least one reinforcing fiber, the at least one reinforcing fiber including a glass core surrounded by a polymer cladding. The polymer cladding can further be surrounded by a tie layer chosen to enhance bonding of the reinforcing fiber with other layers in a catheter assembly.

It is desirable for the at least one reinforcing fiber to be non-magnetically-susceptible and non-electrically-conductive. In embodiments of the instant disclosure, the overall diameter of the at least one reinforcing fiber does not exceed 65 µm, with the diameter of the glass core being between 50 and 55 µm.

It is also contemplated that the glass core can be doped, for example with germanium.

The foregoing and other aspects, features, details, utilities, and advantages of the present invention will be apparent from reading the following description and claims, and from reviewing the accompanying drawings.

DETAILED DESCRIPTION

The instant disclosure provides a catheter shaft suitable for use in the human vasculature for known medical procedures, such as cardiac mapping and ablation. For purposes of illustration, embodiments of the disclosure will be described in connection with an elongate electrophysiology catheter. It is contemplated, however, that the described features and methods may be incorporated into any number of catheters or similar devices (e.g., steerable diagnostic and therapeutic catheters and steerable introducers, fixed curve catheters and introducers, guidewires, and the like), as well as other elongate medical devices where the use of a non-electrically-conductive, non-magnetically-susceptible reinforcing layer would be beneficial.

Figure 1:
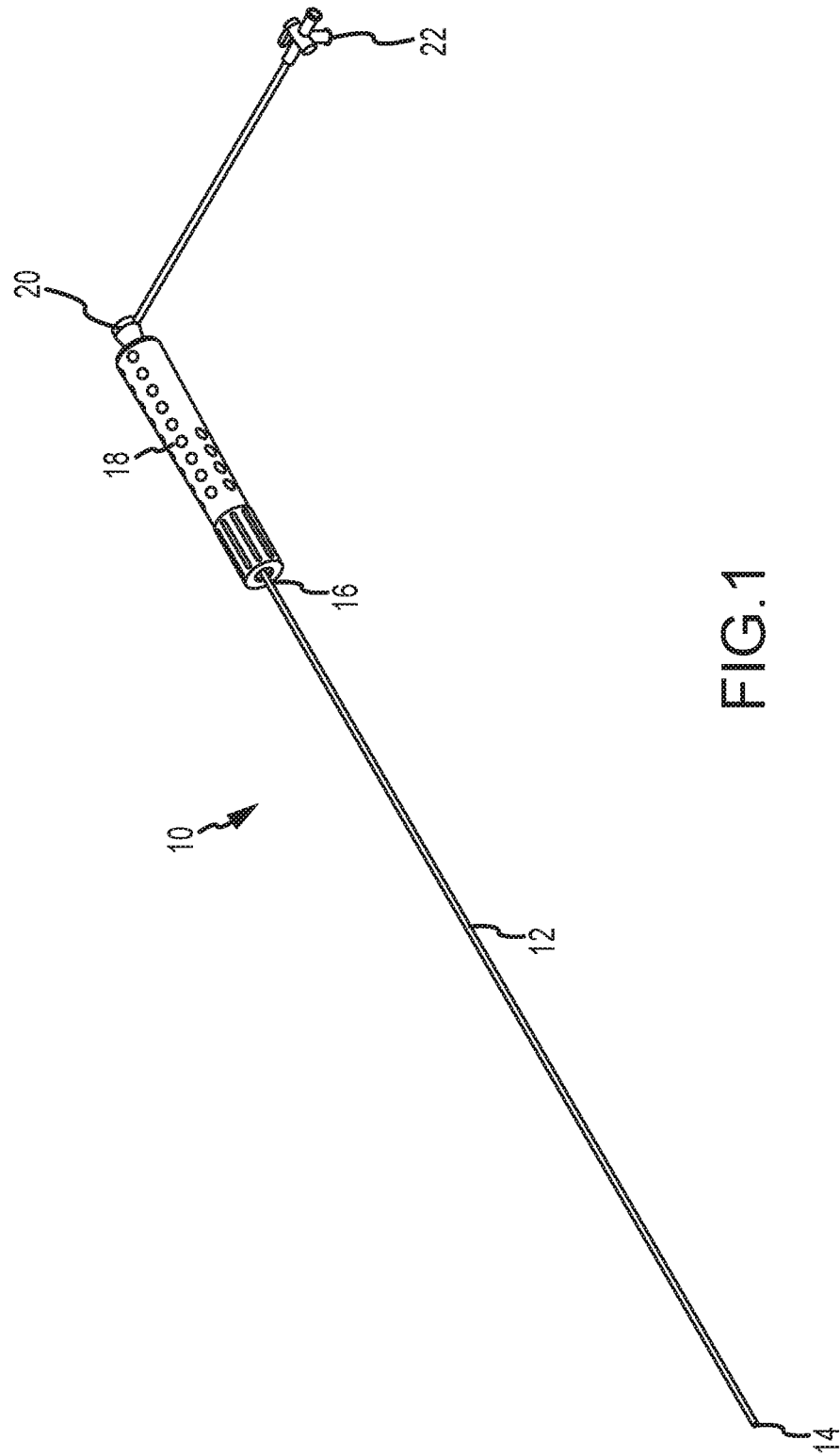
FIG. 1 is a perspective view of an exemplary catheter according to embodiments of the instant disclosure.

Referring now to the figures, and in particular to FIG. 1, an electrophysiology catheter 10 includes a shaft 12 having a distal end 14 and a proximal end 16. Distal end 14 may include one or more diagnostic and/or therapeutic elements such as electrodes (including metallic and/or MRI-compatible electrodes, virtual electrodes, etc.), positioning sensors, pressure sensors, ultrasound transducers, balloons (including cryogenic balloons, virtual electrode balloons, high-intensity focused ultrasound balloons, etc.), and the like. A handle 18 may be coupled to proximal end 16 of shaft 12 to control catheter 10 (e.g., to push and/or torque catheter 10). Catheter 10 may also include a hub 20 operably coupled to an inner lumen 42 (not shown in FIG. 1, but visible in FIG. 5) within handle 18. A valve 22 may be operably connected to hub 20. Of course, it is also contemplated that any known device for manipulation of catheter 10 may be coupled to proximal end 16 thereof, including, without limitation, robotic manipulation devices and the like.

One method of manufacture of catheter 10, and in particular of at least a portion of shaft 12, according to an embodiment of the present disclosure will be described with reference to FIGS. 2-4. As they are assembled, the components of shaft 12 will be collectively referred to as a "catheter shaft assembly."

Figure 2:
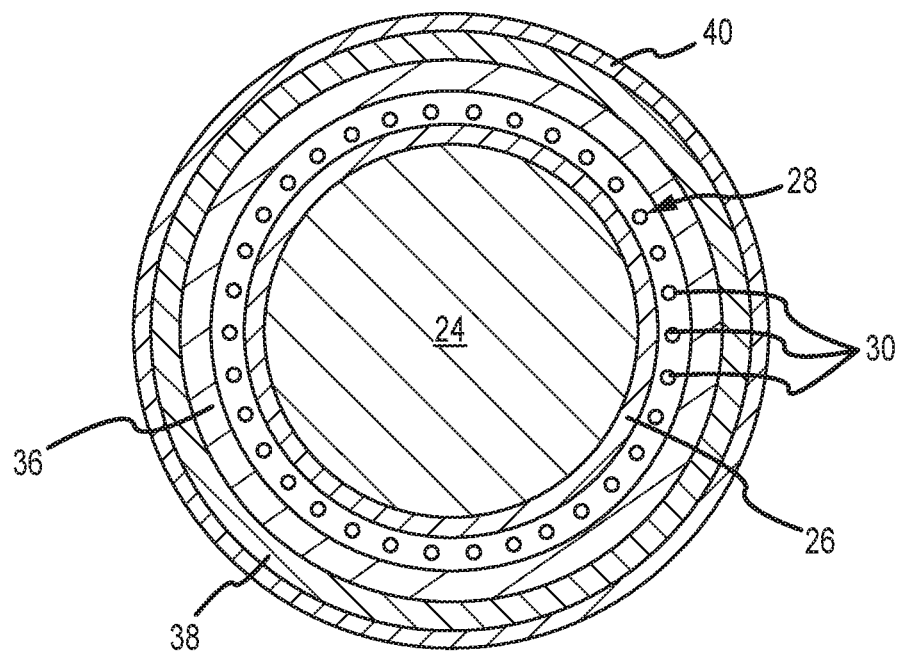
FIG. 2 is a transverse cross-sectional view of the various components of a catheter shaft assembly according to aspects disclosed herein prior to the application of energy to melt process the catheter shaft assembly into a catheter shaft.
Figure 3:
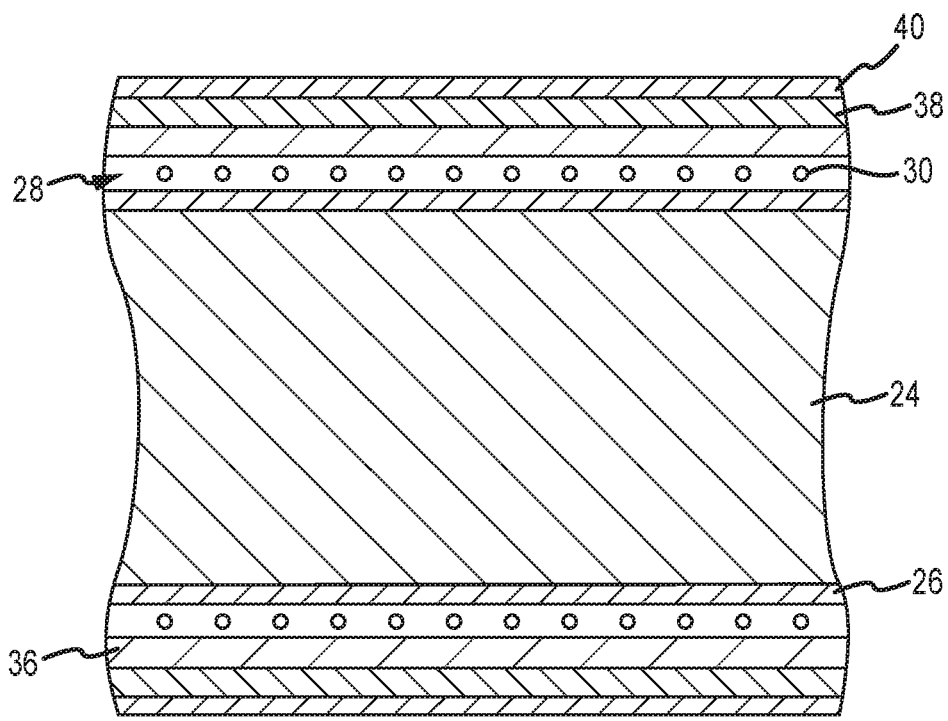
FIG. 3 is a longitudinal cross-sectional view of the various components of a catheter shaft assembly according to aspects disclosed herein prior to the application of energy to melt process the catheter shaft assembly into a catheter shaft.

As depicted in FIGS. 2 and 3, a mandrel or hypotube 24, which can be round in cross-section and from about 6 inches to about 4 feet in length, may be the first component of the catheter shaft assembly during manufacture of catheter shaft 12. Typically, mandrel 24 is disposable. Mandrel 24 has a distal end and a proximal end.

An inner layer 26 is formed about mandrel 24. For example, inner layer 26 may be knotted at one end (e.g., the distal end) and then fed onto mandrel 24. In other aspects of the disclosure, inner layer 26 may be extruded about mandrel 24.

Inner layer 26 may be an extruded polymeric tubing, such as pre-extruded (and optionally chemically-etched) polytetrafluoroethylene (PTFE) tubing (e.g., Teflon® brand tubing). Inner layer 26 may also be made of other melt-processable polymers, including, without limitation, fluorinated ethylene-propylene copolymer (FEP), perfluoroalkoxyethylene (PFA), poly(vinylidene fluoride), poly(ethylene-co-tetrafluoroethylene), and other fluoropolymers with surface treatment such as chemical etching, plasma and corona treatment, and the like. One of ordinary skill will also appreciate that the inner layer 26 may be made of some melt-processable thermoplastic elastomeric polymers with sufficiently high mechanical strength and rigidity (e.g., durometer of at least about 60D), including, without limitation, polyamide-based thermoplastic elastomers (namely poly(ether-block-amide), Pebax®), polyester-based thermoplastic elastomers (e.g., Hytrel®), thermoplastic polyurethanes (e.g., Pellethane®, Estane®), ionic thermoplastic elastomers, functionalized thermoplastic olefins and any combinations thereof. In general, suitable materials for inner layer 26 may also be selected from various thermoplastics, including, without limitation, polyamides, polyurethanes, polyesters, functionalized polyolefins, polycarbonate, polysulfones, polyimides, polyketones, liquid crystal polymers and any combination thereof. Specific suitable materials for inner layer 26 include, without limitation, Pebax® 7233, Pebax® 6333, Grilamid L25, Rilsan AESNO, Rilsan BESNO, Makrolon 3108, Makrolon 1239, and the like.

One or more reinforcing layers 28 may then be formed about inner layer 26. Reinforcing layer(s) 28 may be formed by reinforcing fiber(s) 30.

Figure 4:
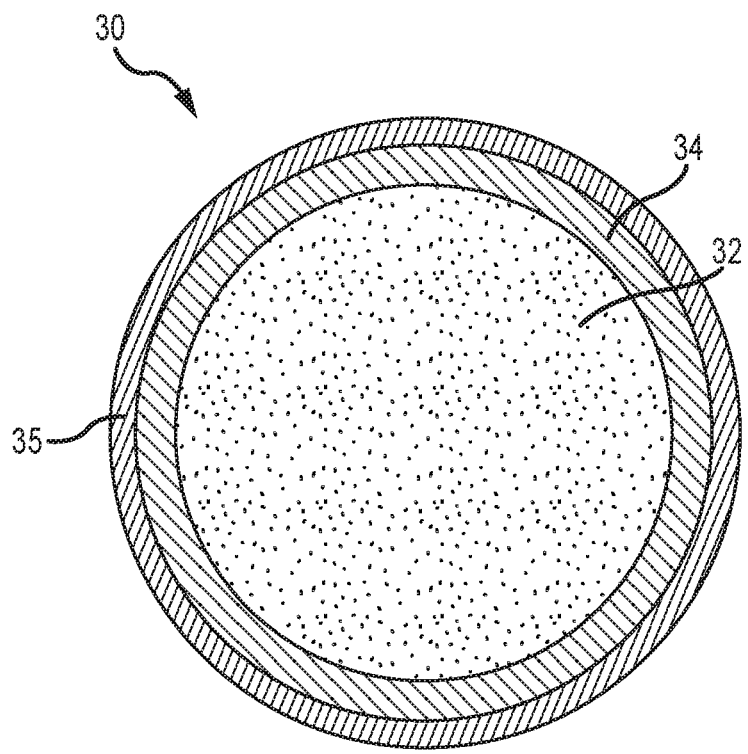
FIG. 4 is a transverse cross-sectional view of a reinforcing fiber as disclosed herein.

FIG. 4 is a transverse cross-section of a representative reinforcing fiber 30. As shown in FIG. 4, reinforcing fiber 30 generally includes a core 32 and a cladding 34. Advantageously, neither core 32 nor cladding 34 includes any electrically-conductive or magnetically-susceptible material (e.g., both core 32 and cladding 34 are non-metallic). As such, reinforcing layer(s) 28 does not interfere with MRI (either in terms of image quality or in terms of experiencing self-heating when subjected to a magnetic field).

In some embodiments of the disclosure, core 32 comprises glass (e.g., silica), while cladding 34 comprises a polymer (e.g., a polyimide, such as silicone or acrylate). In such embodiments, the silica core 32 provides desirable mechanical properties, while cladding 34 can enhance durability and confer biocompatibility upon reinforcing layer(s) 28.

Core 32 can also be doped. For example, in some embodiments of the disclosure, core 32 is doped with germanium.

According to at least one embodiment, reinforcing fiber 30 has an overall diameter of about 65 μm, with core 32 having a diameter of between about 50 and 55 μm.

Suitable materials for reinforcing fiber 30 include, without limitation, Polymicro Technologies™ silica/silica optical fibers from Molex Inc.

Optionally, a tie layer 35 is provided around cladding 34. Tie layer 35 enhances the bonding of reinforcing fiber 30 to outer layers 36, 38, described below. Tie layer 35 can be, for example, a layer of a poly(ether-block-amide), such as Pebax® made by Arkema, Inc., that is about 0.0002" thick.

Reinforcing layer(s) 28 may take various forms. For example, in some embodiments, one or more reinforcing fibers 30 are wound helically about inner layer 26. In other embodiments, one or more reinforcing fibers 30 are braided into a braided reinforcing layer.

Insofar as various configurations for reinforcing layer(s) 28 will be familiar to those of ordinary skill in the art, a detailed description of specific configurations of reinforcing layer(s) 28 is not necessary to an understanding of the instant disclosure. Nonetheless, for purposes of illustration, several exemplary configurations for reinforcing layer(s) 28 are disclosed in U.S. application Ser. Nos. 11/967,219 and 11/967,220, both of which are hereby incorporated by reference as though fully set forth herein.

Reinforcing layer(s) 28 may be formed separately on a disposable core and slipped about inner layer 26. Alternatively, reinforcing layer(s) 28 may be formed directly upon inner layer 26 to form a reinforced inner layer.

It is contemplated that either single thread (e.g., a single length of a polymer clad glass fiber) or multi-thread fibers (e.g., multiple lengths of polymer clad glass fiber grouped together, similar to how braided ropes can be formed) may be used to form reinforcing layer(s) 28. Where multi-thread fibers are used, it is contemplated that the reinforcing fibers 30 can include about eight or more threads (e.g., eight or more separate lengths of polymer clad glass fiber), and more particularly between about ten threads and about thirty threads (e.g., between about ten and about thirty separate lengths of polymer clad glass fiber).

Referring again to FIGS. 2 and 3, one or more outer layers may be formed about reinforcing layer(s) 28. For purposes of illustration, two concentric outer layers 36, 38 are shown in FIGS. 2 and 3. It should be understood, however, that more or fewer outer layers can be used without departing from the scope of the instant disclosure. Similarly, although FIG. 3 depicts outer layers 36, 38 each as one continuous longitudinal segment, it is also contemplated that outer layers 36 and/or 38 can include multiple segments abutting each other along the length of the catheter shaft assembly.

In some embodiments, outer layers 36, 38 are extruded about reinforcing layer(s) 28. In other embodiments of the disclosure, outer layers 36, 38 are separately extruded and then slipped about reinforcing layer(s) 28 as part of the catheter shaft assembly.

Outer layers 36, 38 are typically melt-processable polymeric tubes, such as extruded polytetrafluoroethylene (PTFE) tubing (e.g., Teflon® brand tubing), optionally including surface etching. Outer layers 36, 38 may also be made of other melt processing polymers, including, without limitation, etched polytetrafluoroethylene and other fluoropolymers, poly(ether block amide)s, thermoplastic polyurethanes, polyester-based thermoplastic elastomers, and other thermoplastic elastomers. One such elastomer is Pebax®, made by Arkema, Inc. Pebax of various durometers may be used, including, without limitation, Pebax 30D to Pebax 72D. Of course, one of ordinary skill in the art will recognize that various thermoplastics described as suitable for use as inner layer 26 (e.g., polyamides, polyesters, polycarbonate, polyurethane, polyolefins, polysulfones, polyimides, liquid crystal polymers, aromatic polyketones, and the like) are also generally suitable for use as outer layers 36, 38. One of ordinary skill will also appreciate that the material of outer layers 36, 38 may be different from or the same as the material of inner layer 26, and/or from each other, as desired, and will further appreciate how to select suitable materials for inner layer 26 and outer layers 36, 38 for a particular application of catheter 10.

The thickness of inner layer 26 and outer layers 36, 38 may be the same or different. Further, in some embodiments, it may be desirable for there to be at least partial chemical compatibility between inner layer 26 and outer layers 36, 38. This may promote bonding between the layers of the catheter shaft assembly and reduce the likelihood of strain-induced polymer delamination under manipulation of catheter 10. Such compatibility may be provided by forming inner layer 26 and outer layers 36, 38 of materials whose polarity and/or solubility parameter are similar to each other. Alternatively, or additionally, chemical modifications may be undertaken to achieve at least partial chemical compatibility between these polymeric layers. In other embodiments, one or more of inner layer 26 and outer layers 36, 38 may include a coupling agent, such as silanes, zirconates, titanates, and the like. In still other embodiments, one or more of inner layer 26 and outer layers 36, 38 may include polymeric modifiers or adhesion promoters.

FIGS. 2 and 3 depict cross sections of the catheter shaft assembly including inner layer 26, reinforcing layer 28, and outer layers 36, 38 before forming catheter shaft 12, which may be accomplished by lamination of the various layers by heating (e.g., reflow bonding). In some embodiments, a layer of heat shrink 40 is placed over outermost outer layer 38 as depicted in FIGS. 2 and 3. Heat shrink 40 is preferably a fluoropolymer or polyolefin material such as polytetrafluoroethylene (PTFE) or fluorinated ethylene-propylene copolymer (FEP).

As an alternative to heat shrink tube 40, the catheter shaft assembly may be placed into a suitable mold prior to subsequent processing. Either heat shrink tube 40 or a suitable mold may be generally referred to as a "shape retention structure," so named because it retains the overall shape of the catheter shaft assembly (that is, the generally circular transverse cross-section) during melt-processing.

The catheter shaft assembly may then be melt-processed. Energy (e.g., radiofrequency energy or thermal energy) is applied to the catheter shaft assembly, for example to the outer surface of the catheter shaft assembly, to bond inner layer 26 and outer layers 36, 38 together in a process often referred to as "reflow bonding." Heat shrink tube 40 has a higher melting or softening temperature than inner layer 26 and outer layers 36, 38, such that, during the melting process, heat shrink tube 40 will contract while retaining its tubular shape. The combination of applied energy and pressure exerted by heat shrink tube 40 forces melted inner layer 26 and outer layers 36, 38 to flow and redistribute about the circumference of the catheter shaft assembly and bond together, encapsulating reinforcing layer(s) 28 therebetween.

Once the catheter shaft assembly has cooled, mandrel 24 can be removed, leaving a central lumen 42 (FIG. 5) extending through at least a portion of formed catheter shaft 12. Optionally, heat shrink tube 40 may also be removed, such that outermost outer layer 38 becomes the outermost layer of catheter shaft 12 (though, as a result of the reflow bonding process, the wall of catheter shaft 12 can generally be considered unitary, with no readily-discernable interface between former inner layer 26 and former outer layers 36, 38, particularly where both inner layer 26 and outer layers 36, 38 were of the same material in the first instance).

Figure 5:
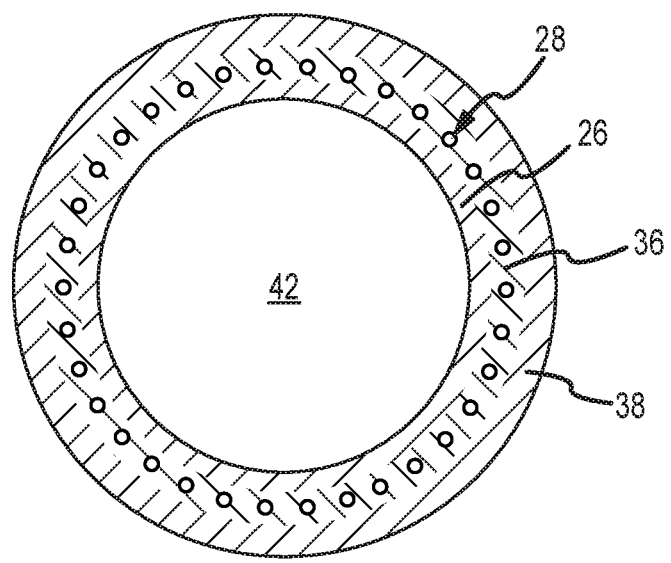
FIG. 5 is a transverse cross-sectional view of a catheter shaft according to embodiments of the disclosure after the application of energy to melt process the catheter shaft assembly into the catheter shaft.

FIG. 5 depicts the catheter shaft assembly after the conclusion of the reflow bonding process (that is, FIG. 5 depicts a transverse cross-section of catheter shaft 12 formed according to an embodiment of the instant disclosure). As described above, as a result of the reflow bonding process described above, reinforcing layer 28 will be encapsulated by inner layer 26 and outer layers 36, 38. Advantageously, and as also discussed above, the interface (e.g., bond) between inner layer 26 and outer layers 36, 38 can be substantially seamless without any dead spaces or material voids covered by reinforcing fiber(s) 30 employed in reinforcing layer(s) 28. This reduces the likelihood of material cracking and other failures of catheter shaft 12.

Although several embodiments have been described above with a certain degree of particularity, those skilled in the art could make numerous alterations to the disclosed embodiments without departing from the spirit or scope of this disclosure.

For example, a catheter formed according to the instant teachings may have varying sizes and varying uses, including, but not limited to, electrophysiological mapping, pacing, the treatment of atrial fibrillation, and the treatment of atrial tachycardia.

One of ordinary skill in the art will also appreciate that other modifications could be made to the catheter shaft assembly herein without departing from the spirit and scope of the disclosure. For example, the catheter shaft assembly could be made steerable, for example as described in U.S. application Ser. No. 11/647,313 ("the '313 application"), or with embedded internal components, for example as described in U.S. application Ser. No. 11/646,578 ("the '578 application"). Both the '313 application and the '578 application are hereby incorporated by reference as though fully set forth herein.

In addition, it is contemplated that a catheter or other elongate medical device according to the teachings herein may be manufactured using alternative techniques. For example, rather than bonding the layers of the catheter shaft assembly via melt-processing (e.g., reflow bonding) as generally described above, one or more layers may be extruded over one another (e.g., extrusion of outer layer 32 over reinforcing layer 28). Where one or more layers are extruded, they may be coextruded.

It is also contemplated to utilize a combination of reflow bonding and extrusion processes.

As another example, the various polymeric layers may be formed by wrapping or winding a suitable material about the catheter shaft assembly (e.g., wrapping surface-etched PTFE tape about mandrel 24 to form inner layer 26).

Additional features of reflow-bonded elongate medical devices that may be applied to good advantage in combination with the teachings herein are described in U.S. Pat. No. 8,734,699, which is hereby incorporated by reference as though fully set forth herein.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A shaft for a medical device configured for use in a human vasculature, the shaft comprising:
    an elongate structure comprising:
        a tubular inner layer;
        a braided reinforcing layer around an outer surface of the tubular inner layer, the reinforcing layer comprising a plurality of reinforcing fibers, wherein each reinforcing fiber of the plurality of reinforcing fibers comprises a glass core surrounded by a polymer cladding; and
        an outer layer bonded to the inner layer such that the reinforcing layer is encapsulated between a material of the outer layer and a material of the inner layer.

2. The shaft according to claim 1, wherein the polymer cladding comprises a polyimide cladding.

3. The shaft according to claim 1, wherein the plurality of reinforcing fibers are non-magnetically-susceptible and non-electrically-conductive.

4. The shaft according to claim 1, wherein the glass core comprises a doped glass core.

5. The shaft according to claim 1, wherein an overall diameter of each reinforcing fiber of the plurality of reinforcing fibers does not exceed 65 μm.

6. The shaft according to claim 5, wherein a diameter of the glass core is between 50 and 55 μm.

* * * * *